United States Patent [19]
Zhang et al.

[11] Patent Number: 5,990,276
[45] Date of Patent: Nov. 23, 1999

[54] SYNTHETIC INHIBITORS OF HEPATITIS C VIRUS NS3 PROTEASE

[75] Inventors: Rumin Zhang, Edison; Philip W. Mui, Freehold, both of N.J.; Patricia C. Weber, Yardley, Pa.

[73] Assignee: Schering Corporation, Kenilworth, N.J.

[21] Appl. No.: 08/853,623

[22] Filed: May 9, 1997

Related U.S. Application Data

[60] Provisional application No. 60/017,470, May 10, 1996.

[51] Int. Cl.$^6$ .............................. C07K 7/00; C07K 7/02; C07K 7/08; C07K 14/00
[52] U.S. Cl. .................... 530/326; 530/327; 530/332; 530/402; 435/183; 435/212; 435/219; 435/236; 514/13; 514/14; 514/15; 930/10; 930/21; 930/30; 930/220
[58] Field of Search .............................. 435/320.1, 69.7, 435/183, 212, 219, 236; 536/23.2, 23.4; 530/326, 327, 332, 402; 514/2, 13–15; 930/10, 21, 30, 220

[56] References Cited

U.S. PATENT DOCUMENTS

| | | | |
|---|---|---|---|
| 5,371,017 | 12/1994 | Houghton et al. | 435/320.1 |
| 5,372,928 | 12/1994 | Miyamura et al. | 435/5 |
| 5,767,233 | 6/1998 | Zhang et al. | 530/326 |
| 5,843,752 | 12/1998 | Dasmahapatra et al. | 435/219 |

FOREIGN PATENT DOCUMENTS

| | | |
|---|---|---|
| WO 95/22985 | 8/1995 | WIPO . |
| WO 96/35717 | 11/1996 | WIPO . |
| WO 96/35806 | 11/1996 | WIPO . |
| WO 96/36702 | 11/1996 | WIPO . |

OTHER PUBLICATIONS

Shimuzu et al (1996) J of Virology, vol. 70 (1) PP. 127–132.
Urbani et al (1996) J Biol. Chem., vol. 272 (14) pp. 9204–9209.
Okamoto et al., 1990, *J. Exp. Med*, 60(3):167–77.
Bartenschlager et al., 1995, *J. Virology*, 69(1):198–205.
Bartenschlager et al., 1994, *J. Virology*, 68(8):5045–55.
Bourdon et al., 1991, *FEBS*, 294(3):163–66.
Failla et al., 1995, *J. Virology*, 69(3):1769–77.
Lin et al., 1994, *J. Virology*, 68(12):9147–57.
Maraganore et al., 1990, *Biochemistry*, 29:7095–7101.
Parry et al., 1994, *Biochemistry*, 33:14807–14.
Pizzi et al., 1994, *PNAS*, 91:888–92.
Tanji et al., 1995, *J. Virology*, 69(3):1575–81.

*Primary Examiner*—Mary E. Mosher
*Attorney, Agent, or Firm*—Jaye P. McLaughlin

[57] ABSTRACT

An inhibitor of the HCV NS3 protease. The inhibitor is a subsequence of a substrate of the NS3 protease or a subsequence of the NS4A cofactor. Another inhibitor of the present invention contains a subsequence of a substrate linked to a subsequences of the NS4A cofactor. In another embodiment the inhibitor is a bivalent inhibitor comprised of a subsequence, a mutated subsequence or a mutated full-length of a substrate of the NS3 protease linked to a subsequence, a mutated subsequence or a mutated full-length suquence of the HCV NS4A cofactor.

7 Claims, 7 Drawing Sheets

SYNTHETIC INHIBITORS OF HEPATITIS C VIRUS NS3 PROTEASE

This filing is a conversion of Provisional U.S. patent applications U.S. Ser. No. 60/017,470, filed May 10, 1996, to a U.S. Utility Patent Application.

BACKGROUND OF THE INVENTION

Hepatitis C virus (HCV) is considered to be the major etiological agent of non-A non-B (NANB) hepatitis, chronic liver disease, and hepatocellular carcinoma (HCC) around the world. The viral infection accounts for greater than 90% of transfusion-associated hepatitis in U.S. and it is the predominant form of hepatitis in adults over 40 years of age. Almost all of the infections result in chronic hepatitis and nearly 20% develop liver cirrhosis.

The virus particle has not been identified due to the lack of an efficient in vitro replication system and the extremely low amount of HCV particles in infected liver tissues or blood. However, molecular cloning of the viral genome has been accomplished by isolating the messenger RNA (mRNA) from the serum of infected chimpanzees then cloned using recombinant methodologies. [Grakoui A. et al. *J. Virol.* 67: 1385–1395 (1993)] It is now known that HCV contains a positive strand RNA genome comprising approximately 9400 nucleotides, whose organization is similar to that of flaviviruses and pestiviruses. The genome of HCV, like that of flavi- and pestiviruses, encodes a single large polyprotein of about 3000 amino acids which undergoes proteolysis to form mature viral proteins in infected cells.

Cell-free translation of the viral polyprotein and cell culture expression studies have established that the HCV polyprotein is processed by cellular and viral proteases to produce the putative structural and nonstructural (NS) proteins. At least nine mature viral proteins are produced from the polyprotein by specific proteolysis. The order and nomenclature of the cleavage products are as follows: $NH_2$-C-E1-E2-NS2-NS3-NS4A-NS4B-NS5A-NS5B-COOH. The three amino terminal putative structural proteins, C (capsid), E1, and E2 (two envelope glycoproteins), are believed to be cleaved by host signal peptidases of the endoplasmic reticulum(ER). The host enzyme is also responsible for generating the amino terminus of NS2. The proteolytic processing of the nonstructural proteins are carried out by the viral proteases: NS2-3 and NS3, contained within the viral polyprotein. The NS2-3 protease catalyzes the cleavage between NS2 and NS3. It is a metalloprotease and requires both NS2 and the protease domain of NS3. The NS3 protease catalyzes the rest of the cleavages of the substrates in the nonstructural part of the polyprotein. The NS3 protein contains 631 amino acid residues and is comprised of two enzymatic domains: the protease domain contained within amino acid residues 1-181 and a helicase ATPase domain contained within the rest of the protein. It is not known if the 70 kD NS3 protein is cleaved further in infected cells to separate the protease domain from the helicase domain, however, no cleavage has been observed in cell culture expression studies.

The NS3 protease is a member of the serine proteinase class of enzymes. It contains His, Asp, and Ser as the catalytic triad. Mutation of the catalytic triad residues abolishes the cleavages at substrates NS3/4A, NS4A/4B, NS4B/5A, and NS5A/5B. The cleavage between NS3 and NS4A is mediated through an intramolecular enzymatic reaction, whereas the cleavages at NS4A/4B, 4B/5A, 5A/5B sites occur in a trans enzymatic reaction.

Experiments using transient expression of various forms of HCV NS polyproteins in mammalian cells have established that the NS3 serine protease is necessary but not sufficient for efficient processing of all these cleavages. Like flaviviruses, the HCV NS3 protease also requires a cofactor to catalyze some of these cleavage reactions. In addition to the serine protease NS3, the NS4A protein is absolutely required for the cleavage of the substrate at the NS3/4A and 4B/5A sites and increases the efficiency of cleavage of the substrate between 5A/5B, and possibly 4A/4B.

Because the HCV NS3 protease cleaves the non-structural HCV proteins which are necessary for the HCV replication, the NS3 protease can be a target for the development of therapeutic agents against the HCV virus. Thus there is a need for the development of inhibitors of the HCV protease.

SUMMARY OF THE INVENTION

The present invention fills this need by providing for a bivalent inhibitor of an hepatitis C NS3 protease comprised of a first peptide linked to a second peptide, said first peptide being a subsequence, mutated subsequence or a mutated full-length sequence of a substrate of the hepatitis C NS3 protease and said second peptide being a subsequence, a mutated subsequence or a mutated full-length sequence of a hepatitis C NS4A polypeptide.

The present application further provides for an inhibitor of an HCV protease comprised of a peptide, said peptide being a subsequence, a mutated subsequence, or a mutated full-length sequence of a substrate of the HCV NS3 protease.

The present application further provides for an inhibitor of an HCV NS3 protease comprised of a peptide, said peptide being a subsequence, a mutated subsequence or a mutated full-length sequence of an HCV NS4A polypeptide.

The present invention further comprises a method for treating an individual infected with the HCV virus comprising administering an inhibitor of an HCV NS3 protease to said individual, said inhibitor being comprised of a first peptide linked to a second peptide, said first peptide being a subsequence, a mutated subsequence or a mutated full-length sequence of a substrate of the hepatitis C NS3 protease and said second peptide being a subsequence, a mutated subsequence or a mutated full-length sequence of a hepatitis C NS4A polypeptide.

The present invention further comprises a method for treating an individual infected with the HCV virus comprising administering an inhibitor of an HCV NS3 protease to said individual, said inhibitor being comprised of a peptide, said peptide being a subsequence, a mutated subsequence or a mutated full-length sequence of a substrate of the HCV NS3 protease.

The present invention further comprises a method for treating an individual infected with the HCV virus comprising administering an inhibitor of an HCV NS3 protease to said individual, said inhibitor being comprised of a peptide, said peptide being a subsequence, a mutated subsequence or a mutated full-length sequence of an HCV NS4A polypeptide.

The present invention further comprises a pharmaceutical composition for treating an individual infected with hepatitis C virus, said pharmaceutical composition being an inhibitor of an HCV NS3 protease, said inhibitor being comprised of a first peptide linked to a second peptide, said first peptide being a subsequence, a mutated subsequence or a mutated full-length sequence of a substrate of the hepatitis C NS3 protease and said second peptide being a subsequence, a mutated subsequence or a mutated full-length sequence of a hepatitis C NS4A polypeptide, and a pharmaceutical carrier.

The present invention further provides for a pharmaceutical composition for treating an individual infected with hepatitis C virus, said pharmaceutical composition being comprised of an inhibitor of an HCV NS3 protease and a pharmaceutical carrier, said inhibitor being a subsequence, a mutated subsequence or a mutated full-length sequence of a substrate of the HCV NS3 protease.

The present invention further provides for a pharmaceutical composition for treating an individual infected with hepatitis C virus, said pharmaceutical composition being comprised of an inhibitor of an HCV NS3 protease and a pharmaceutical carrier, wherein said inhibitor is comprised of a peptide, said peptide being a subsequence, a mutated subsequence or a mutated full-length subsequence of an HCV NS4A polypeptide.

DETAILED DESCRIPTION OF THE INVENTION

The teachings of all references cited are incorporated herein in their entirety by reference.

The present invention are inhibitors of the HCV NS3 protease. The present invention relates to inhibitors of the HCV NS3 protease which inhibit either the interaction of a substrate or cofactor NS4A with the NS3 protease or a bivalent inhibitor which inhibits the interaction of the NS3 protease with both cofactor NS4A and a substrate of the NS3 protease. Compared to inhibitors targeting only at a single binding site, bivalent enzyme inhibitors may provide additional advantages in terms of higher binding affinity (potency), as well as enhanced specificity against similar cellular host enzymes for reduced toxicity effects.

Design Strategy of Bivalent Inhibitors of HCV NS3 Protease

The basic strategy for the design of bivalent inhibitors of HCV NS3 protease involved the devise of a molecular framework consisting of three individual components:

1. a region appropriate for binding to a substrate binding site;
2. a region suitable for binding to the NS4A binding site;
3. a flexible linker region connecting regions (1) and (2) which would allow the two end regions to bind to their respective binding sites.

Figure 1:
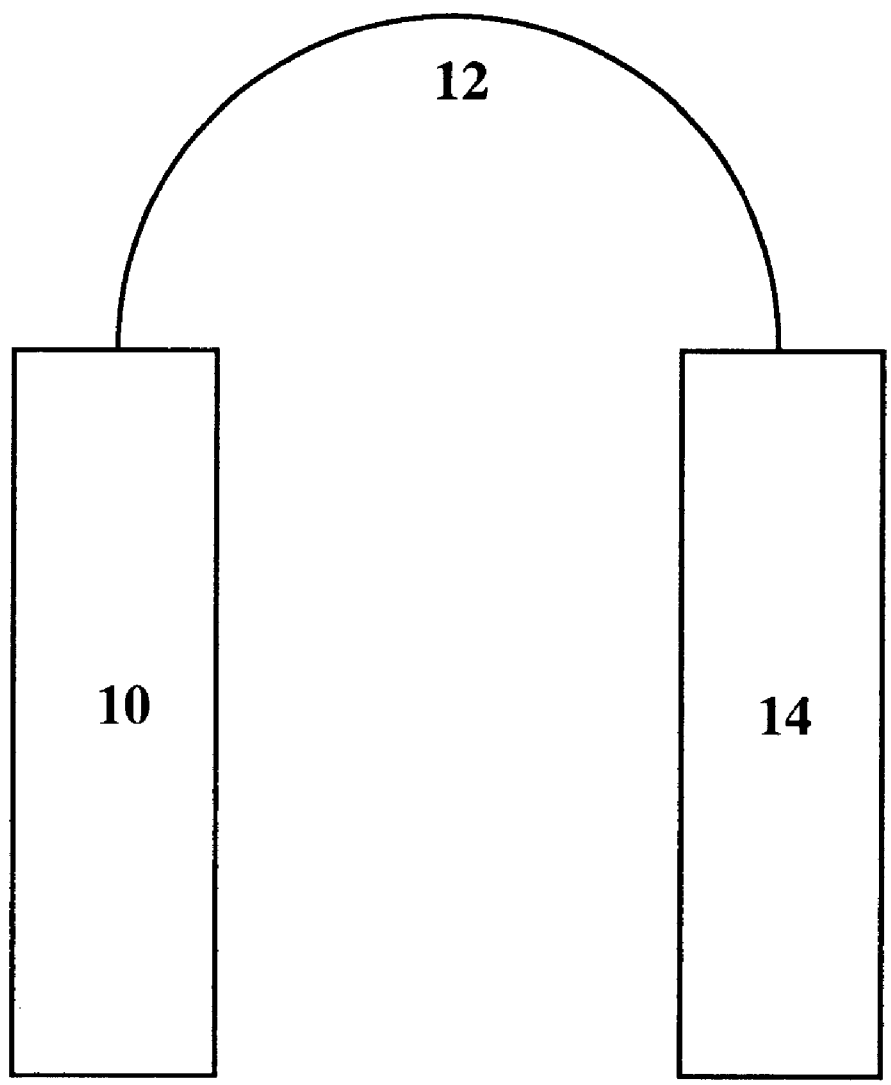
FIG. 1 schematically depicts an embodiment of a bivalent inhibitor of the present invention.

Schematically, this is represented by FIG. 1 in which the substrate subsequence is depicted as block, 10, being attached to linker 12, and said linker 12 being attached to the polypeptide NS4A designated 14.

Since the NS3 protease cleaves the HCV polyprotein at the NS3/4A, 4A/4B, 4B/5A and 5A/5B junctions, then subsequences of or mutated subsequences of these sites can be used as substrate inhibitors. A substrate inhibitor which is a subsequence of the inhibitor should be a subsequence which is prior to or after the cleavage site but preferably should not contain the cleavage site. A mutated subsequence or mutated full-length sequence of the substrate can be used if the cleavage site is mutated so that the cleavage of the substrate does not occur cleavage leads to mechanism-based inactivation of the protease.

For example, the NS3/4A cleavage site contains the following sequence:

```
Cys Met Ser Ala Asp Leu Glu Val Val Thr Ser Thr Trp Val Leu   (SEQ. ID NO.:26)
              5                   10                  15
        Val Gly Gly Val Leu
                         20
```

The cleavage site is between the threonine at position 10 and the serine at position 11. Any subsequence inhibitor should preferably be before the serine or after the threonine residue. Alternatively, a mutated subsequence or sequence can be produced by changing the threonine/serine cleavage site at position 10-11 to eliminate the cleavage site.
NS4A/4B contains the following sequence.

```
Tyr Gln Glu Phe Asp Glu Met Glu Glu Cys Ser Gln His Leu Pro   (SEQ ID NO.:27)
              5                   10                  15
        Tyr Ile Glu Gln Gly.
                         20
```

The cleavage site is between the cysteine residue at position 10 and the serine at position 11. Any subsequence should preferably be before the serine or after the cysteine, but should preferably not contain both the cysteine and the serine. Alternatively, a mutated subsequence or sequence can be produced by changing the cysteine/serine cleavage site at position 10-11 to eliminate the cleavage site.
NS4B/5A contains the following sequence.

```
Trp Ile Ser Ser Glu Cys Thr Thr Pro Cys Ser Gly Ser Trp Leu   (SEQ ID NO.:28)
              5                   10                  15
        Arg Asp Ile Trp Asp
                         20
```

The cleavage site is between the cysteine at position 10 and serine at position 11. Any subsequence should preferably end before the serine or start after the cysteine but should preferably not contain both the serine and the cysteine.

Alternatively, a mutated subsequence or sequence can be produced by changing the cysteine/serine cleavage sit at position 10-11 to eliminate the cleavage site.

NS5A/5B contains the following sequence.

```
Asp Thr Glu Asp Val Val Cys Cys Ser Met Ser Tyr Thr Trp Thr (SEQ. ID NO.:25)
              5                   10                  15
Gly
10
```

The cleavage site is between the cysteine at position 8 and the serine at position 9. Any subsequence should preferably end at the cysteine or start at the serine, but should preferably not contain both the cysteine and the serine. Alternatively, a mutated sequence or subsequence can be produced by changing the cysteine/serine cleavage site at position 8-9 to eliminate the cleavage site.

Linker 12 can be any chemical entity that can form a bond with polypeptides 10 and 14. Preferably the linker should be equivalent in length to a carbon chain having about 7–14 carbon atoms. Examples of suitable linkers are two 6-aminocaproic acid (Acp) residues or an Acp and Lys wherein one of the polypeptides 10 or 14 form a peptide bond with the ε amine of lysine.

Examples of bivalent inhibitors of the present invention are the following:

Glu-Asp-Val-Val-Cys-Cys-Acp-Acp-Cys-Val-Val-Ile-Val-Gly-Arg-Ile-Val-Leu-Ser-Gly-Lys (SEQ ID NO: 1)

Glu-Asp-Val-Val-Cys-Cys-Acp-Cys-Val-Val-Ile-Val-Gly-Arg-Ile-Val-Leu-Ser-Gly-Lys-Lys (SEQ ID NO:2)

Glu-Asp-Val-Val-Cys-Cys-Acp-Xaa-Lys-Gly-Ser-Leu-Val-Ile-Arg-Gly-Val-Ile-Val-Val-Cys (SEQ ID NO: 3)

wherein Xaa is a lysine residue having a peptide bond between its ε-amino and the carboxyl group of the following lysine which forms a peptide bond with the glycine at position 10. Furthermore, the glutamic acid residue at position 1 may or may not be acetylated.

Glu-Asp-Val-Val-Cys-Cys-Xaa-Lys-Gly-Ser-Leu-Val-Ile-Arg-Gly-Val-Ile-Val-Val-Cys (SEQ ID NO: 4)

wherein Xaa is Lysine having a peptide bond between its ε-amino and the carboxyl group of the following lysine which forms a peptide bond with the Gly; furthermore, the carboxyl group of the Xaa forms a peptide bond with the α-amino group of another lysine (not shown);

Glu-Asp-Val-Val-Cys-Cys-Acp-Acp-Lys-Gly-Ser-Leu-Val-Ile-Arg-Gly-Val-Ile-Val-Val-Cys (SEQ ID NO: 5)

wherein the amino acids at positions 9–21 are preferably D-amino acids;

Glu-Asp-Val-Val-Cys-Cys-Acp-Lys-Cys-Val-Val-Ile-Val-Gly-Arg-Ile-Val-Leu-Ser-Gly-Lys (SEQ ID NO: 6)

wherein the lysine residue at position 8 has a peptide bond between the carboxyl of Acp and the α amino group of the lysine, and the ε amino group of the lysine at position 8 forms a peptide bond with the carboxyl group of the cysteine residue at position 9 and the amino acid residues at positions 9–21 are preferably D-amino acid residues;

Glu-Asp-Val-Val-Cys-Cys-Acp-Lys-Gly-Ser-Leu-val-Ile-Arg-Gly-Val-Ile-Val-Val-Cys-Lys (SEQ ID NO: 7)

wherein amino acid residues at positions 8–20 are preferably D-amino acid residues;

Glu-Asp-Val-Val-Cys-Cys-Xaa-Cys-Val-Val-Ile-Val-Gly-Arg-Ile-Val-Leu-Ser-Gly-Lys (SEQ ID NO: 8)

wherein Xaa is a Lys which forms a peptide bond between its ε-amino acid and the carboxyl group of the Cys residue at position 8 and the carboxyl group of the Lys residue forms a peptide bond with an alpha amino group of another Lys residue (not shown), preferably the amino acid residues at positions 8–20 are D-amino acids.

Examples of suitable monovalent inhibitors of the present invention are the following:

Lys-Gly-Ser-Leu-Val-Ile-Arg-Gly-Val-Ile-Val-Val-Cys-Lys (SEQ ID NO.: 9)

wherein the amino acid residues at positions 1–13 are preferably D-amino acid residues;

Lys-Gly-Ser-Leu-Val-Ile-Arg-Gly-Val-Ile-Val-Lys (SEQ ID NO.: 10)

wherein amino acid residues at positions 1–11 are preferably D-amino acid residues;

Cys-Val-Val-Ile-Val-Gly-Arg-Ile-Val-Leu-Ser-Gly-Lys (SEQ ID NO.: 11)

wherein the amino acid residues are preferably D-amino acid residues;

Ser-Leu-Val-Ile-Arg-Gly-Val-Ile-Val (SEQ ID NO.: 12)

wherein the amino acid residues are preferably D-amino acid residues and the serine residue at position 1 has been preferably acetylated;

Lys-Gly-Ser-Leu-Val-Ile-Arg-Gly-Val-Ile-Val-Val-Cys (SEQ ID NO.: 13)

wherein the amino acid residues are preferably D-amino acid residues the lysine residue at position 1 is preferably acetylated;

Xaa-Lys-Gly-Ser-Leu-Val-Ile-Arg-Gly-Val-Ile Val-Val-Cys-Lys-Lys (SEQ ID NO.: 14);

wherein Xaa is biotin and the amino acid residues at positions 2–14 are preferably D-amino acid residues;

Lys-Gly-Ser-Leu-Val-Ile-Arg-Gly-Val-Ile-Val-Val-Cys-Xaa-Lys (SEQ ID NO.: 15);

Xaa is a lysine residue in which the ε amino group of the lysine forms a peptide bond with a biotin, and amino acid residues at positions 1–13 are preferably D-amino acid residues.

The inhibitors of the present invention can be synthesized by a suitable method such as by exclusive solid phase synthesis, partial solid phase methods, fragment condensation or classical solution synthesis. The polypeptides are preferably prepared by solid phase peptide synthesis as described by Merrifield, J. Am. Chem. Soc. 85:2149 (1963). The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexyloxycarbonyl] and alkyl type protecting groups (e.g., benzyl, triphenylmethyl). The preferred protecting groups are tBoc and Fmoc, thus the peptides are said to be synthesized by tBoc and Fmoc chemistry, respectively.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide. In tBoc chemistry, the side-chain protecting groups for trifunctional amino acids are mostly benzyl based. In Fmoc chemistry, they are mostly tert.-butyl or trityl based.

In tBoc chemistry, the preferred side-chain protecting groups are tosyl for Arg, cyclohexyl for Asp, 4-methylbenzyl (and acetamidomethyl) for Cys, benzyl for Glu, Ser and Thr, benzyloxymethyl (and dinitrophenyl) for His, 2-Cl-benzyloxycarbonyl for Lys, formyl for Trp and 2-bromobenzyl for Tyr. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for Arg, trityl for Asn, Cys, Gln and His, tert-butyl for Asp, Glu, Ser, Thr and Tyr, tBoc for Lys and Trp.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) is used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al (1984)., "Solid Phase Peptide Synthesis" (2nd Edition), Pierce Chemical Co., Rockford, Ill.; and Bayer & Rapp (1986) *Chem. Pept. Prot.* 3, 3; and Atherton, et al. (1989) *Solid Phase Peptide Synthesis: A Practical Approach*, IRL Press, Oxford.

The C-terminal amino acid, protected at the side-chain if necessary and at the alpha-amino group, is attached to a hydroxylmethyl resin using various activating agents including dicyclohexylcarbodiimide (DCC), N,N'-diisopropylcarbodiimide DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions Following the attachment to the resin support, the alpha-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluorophosphate (BOP) and its pyrrolidine analog (PyBOP), bromo-tris-pyrrolidino-phosphonium hexafluorophosphate (PyBroP), N-[(1H-benzotriazol-1-yl)-(dimethylamino) methylene]-N-methylmethanaminium hexaflourophosphate N-oxide (HBTU) and its tetrafluoroborate analog (TBTU) or its pyrrolidine analog (HBPyU), (HATU) and its tetrafluoroborate analog (TATU) or pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Amino acid flourides or chlorides may be used for difficult couplings. Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction can be monitored at each stage, e.g., by the ninhydrin reaction as described by Kaiser et al., *Anal. Biochem.* 34:595 (1970). In cases where incomplete coupling is found, the coupling reaction is extended and repeated and may have chaotropic salts added. The coupling reactions can be performed automatically with commercially available instruments such as ABI model 430A, 431A and 433A peptide synthesizers.

After the entire assembly of the desired peptide, the peptide-resin is cleaved with a reagent with proper scavengers. The Fmoc peptides are usually cleaved and deprotected by TFA with scavengers (e.g., $H_2O$, ethanedithiol, phenol and thioanisole). The tBoc peptides are usually cleaved and deprotected with liquid HF for 1–2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of Trp and dinitrophenyl group of His need to be removed, respectively, by piperidine and thiophenol in DMF prior to the HF cleavage. The acetamidomethyl group of Cys can be removed by mercury(II) acetate and alternatively by iodine, thallium (III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

In particular the peptides of the present invention were assembled from a Fmoc-Amide resin or a Fmoc-L-Lys-(tBoc)—Wang resin on an ABI model 433A synthesizer (Applied Biosystems, Foster City, Calif.) by solid phase peptide synthesis method as originally described by Merrifield, J. Am. Chem. Soc. 85:2149 (1963) but with Fmoc chemistry. The side chains of trifunctional amino acids were protected by tert.-butyl for Glu, Asp and Ser, trityl for Cys, tert.-butyloxycarbonyl (tBoc) for Lys and 2,2,5,7,8-pentamethylchroman-6-sulfonyl (Pmc) or 2,2,4,6, 7-pentamethyldihydrobenzofuran-5-sulfonyl (Pbf) for Arg. N-a-Fmoc protected amino acids were pre-activated by HATU and 1-hydroxy-7-azabenzotriazole (HOAt) prior to coupling to the resin. Dimethylsulfoxide (20%) was added during conditional extended coupling and Fmoc deprotection reactions. The synthesis of the inhibitors SEQ ID NOs: 1, 2, 5, 7, and 9–15 was accomplished by sequential and linear assembly of appropriate D- and L-amino acids and achiral amino acids (Gly and Ahx). The synthesis of the inhibitors SEQ ID NOs: 3, 4, 6, and 8 required orthogonal chain assembly anchored at a Lys residue whose side chain amino group was protected by 1-(4,4-dimethyl-2,6-dioxocyclohex-1-ylidene)-ethyl (Dde). For example, for the preparation of the inhibitor SEQ ID NO: 3, Ac-Glu-Asp-Val-Val-Cys-Cys-Acp-Lys-(Amide resin) (SEQ ID NO: 29) was first assembled. Then the Dde protecting group on the Lys residue was removed by 2% hydrazine in dimethylformamide (Bycroft, B. W. et al J. Chem. Soc. Chem. Commun. 1993, 778). Finally the second arm Cys-Val-Val-Ile-Val-Gly-Arg-Ile-Val-Leu-Ser-Gly-Lys (SEQ ID NO:30) was sequentially assembled from the side chain amino group. The assembled peptide was cleaved from the resin with simultaneous deprotection of side chain protecting groups for three hours with trifluoroacetic acid (TFA) with proper scavengers (80% TFA: 4% phenol: 4% $H_2O$, 4% thioanisole:4% ethanedithiol: 4% triisopropylsilane). The cleaved peptide was separated from the resin by filtration and precipitated and repeatedly washed in anhydrous ethyl ether. The precipitated peptide was lyophilized in $H_2O$ overnight. The lyophilized crude peptide was purified by reverse phase HPLC. The purified peptide was further analyzed by HPLC, mass spectroscopy and amino acid analysis.

One can ascertain if a potential compound is effective as an inhibitor of the HCV NS3 protease by using a high throughput assay utilizing the NS3 protease, the NS4 cofactor and the peptide substrates, either 4B/5A or 5A/5B. These can be used to screen for compounds which inhibit proteolytic activity of the protease. One does this by developing techniques for determining whether or not a compound will inhibit the NS3 protease from cleaving the viral substrates. If the substrates are not cleaved, the virus cannot replicate. One example of such a high throughput assay is the scintillation proximity assay (SPA). SPA technology involves the use of beads coated with scintillant. Bound to the beads are acceptor molecules such as antibodies, receptors or enzyme substrates which interact with ligands or enzymes in a reversible manner.

For a typical SPA based protease assay the substrate peptide is biotinylated at one end and the other end is radiolabelled with low energy emitters such as $^{125}I$ or $^{3}H$. The labeled substrate is then incubated with the enzyme. Avidin coated SPA beads are then added which bind to the biotin. When the substrate peptide is cleaved by the protease, the radioactive emitter is no longer in proximity to the scintillant bead and no light emission takes place. Inhibitors of the protease will leave the substrate intact and can be identified by the resulting light emission which takes place in their presence.

Another example of a suitable assay technique is an HPLC assay in which the resultant reaction mixture containing the NS3 protease, the substrate products and the potential inhibitor is resolved on an HPLC column to determine the extent of the cleavage of the substrate. If the substrate has not been cleaved or the cleavage has been inhibited, then only the intact substrate would be present or a reduced amount of the cleaved product will be shown to be present. If this is the case, then the compound is an effective inhibitor of the NS3 protease.

Pharmaceutical Compositions

The dosage level of inhibitors necessary for effective therapy to inhibit the HCV NS3 protease will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. See also Langer (1990) *Science* 249:1527–1533. Pharmaceutically acceptable carriers will include water, saline, buffers, and other compounds described, e.g., in the *Merck Index*, Merck & Co., Rahway, N.J. 1µg per kilogram weight of the patient to 500 mg per kilogram weight of the patient with an appropriate carrier is a range from which the dosage can be chosen. Slow release formulations, or a slow release apparatus will often be utilized for continuous administration.

The inhibitors of the HCV NS3 protease of the present invention may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press, Parrytown, N.Y.; *Remington's Pharmaceutical Sciences*, 17th ed. (1990), Mack Publishing Co., Easton, Pa.; Avis, et al. (eds.)(1993) *Pharmaceutical Dosage Forms: Parenteral Medications* 2d ed., Dekker, N.Y.; Lieberman, et al. (eds.)(1990) *Pharmaceutical Dosage Forms: Tablets* 2d ed., Dekker, N.Y.; and Lieberman, et al. (eds.)(1990) *Pharmaceutical Dosage Forms: Disperse Systems* Dekker, N.Y. The therapy of this invention may be combined with or used in association with other chemotherapeutic or chemopreventive agents.

The following examples are included to illustrate but not to limit the present invention.

EXAMPLE 1

Bivalent Inhibitors of HCV NS3 Protease

The bivalent inhibitors of defined by SEQ ID NOs.: 1–10 were synthetically produced as described above and tested for their ability to inhibit the HCV NS3 protease as follows.

Into an aqueous solution containing 25 mM TRIS, 50 mM NaCl, 0.5 mM EDTA, 10% glycerol and 0.1% NP40 was placed the potential inhibitor, the HCV NS3 protease at a concentration of 0.05 µM–0.1 mM, the HCV NS4A cofactor at a concentration of 0.05 µM–0.1 µM and the 5A/5B substrate at a concentration of 50 µM. This solution was then incubated for approximately 2 hours at 30° C. after which the solution was applied to an HPLC to determine if the 5A/5B remained intact and thus the compound was determined to be an inhibitor. However, if the HPLC showed that 5A and 5B were present without the 5A/5B then the compound is not an inhibitor. The potential inhibitors were assayed at several different concentrations to determine the concentration which produced 50% inhibition of the HCV NS3 protease. The results are shown below.

| Inhibitor | IC$_{50}$ (µM) |
| --- | --- |
| SEQ ID NO: 1 50571-120 | 0.6 |
| SEQ ID NO: 2 50962-13 | 3.0 |
| SEQ ID NO: 3 50828-001 | 3.0 |
| SEQ ID NO: 4 50962-22 | 3–30 |
| SEQ ID NO: 5 50571-144 | 0.2 |
| SEQ ID NO: 6 50571-150 | 2.0 |
| SEQ ID NO: 7 50828-131 | 0.2 |
| SEQ ID NO: 8 50962-24 | 0.2 |

EXAMPLE 2

Monovalent Inhibitors of the HCV NS3 Protease

Examples of monovalent inhibitors of the HCV NS3 protease are as follows.

| Inhibitor | IC$_{50}$ (µM) |
| --- | --- |
| SEQ ID NO.: 9 50828-129 | 0.2 |
| SEQ ID NO.: 10 50962-004 | 5 |
| SEQ ID NO.: 11 50828-70 | 0.2 |
| SEQ ID NO.: 12 50828-116 | 0.6 |
| SEQ ID NO.: 13 50571-147 | 2.0 |
| SEQ ID NO.: 14 50962-047 | 0.4 |
| SEQ ID NO.: 15 50962-050 | 0.4 |

EXAMPLES 3

Production of HCV NS3 Protease

A. Plasmid Constructions.

Figure 2:
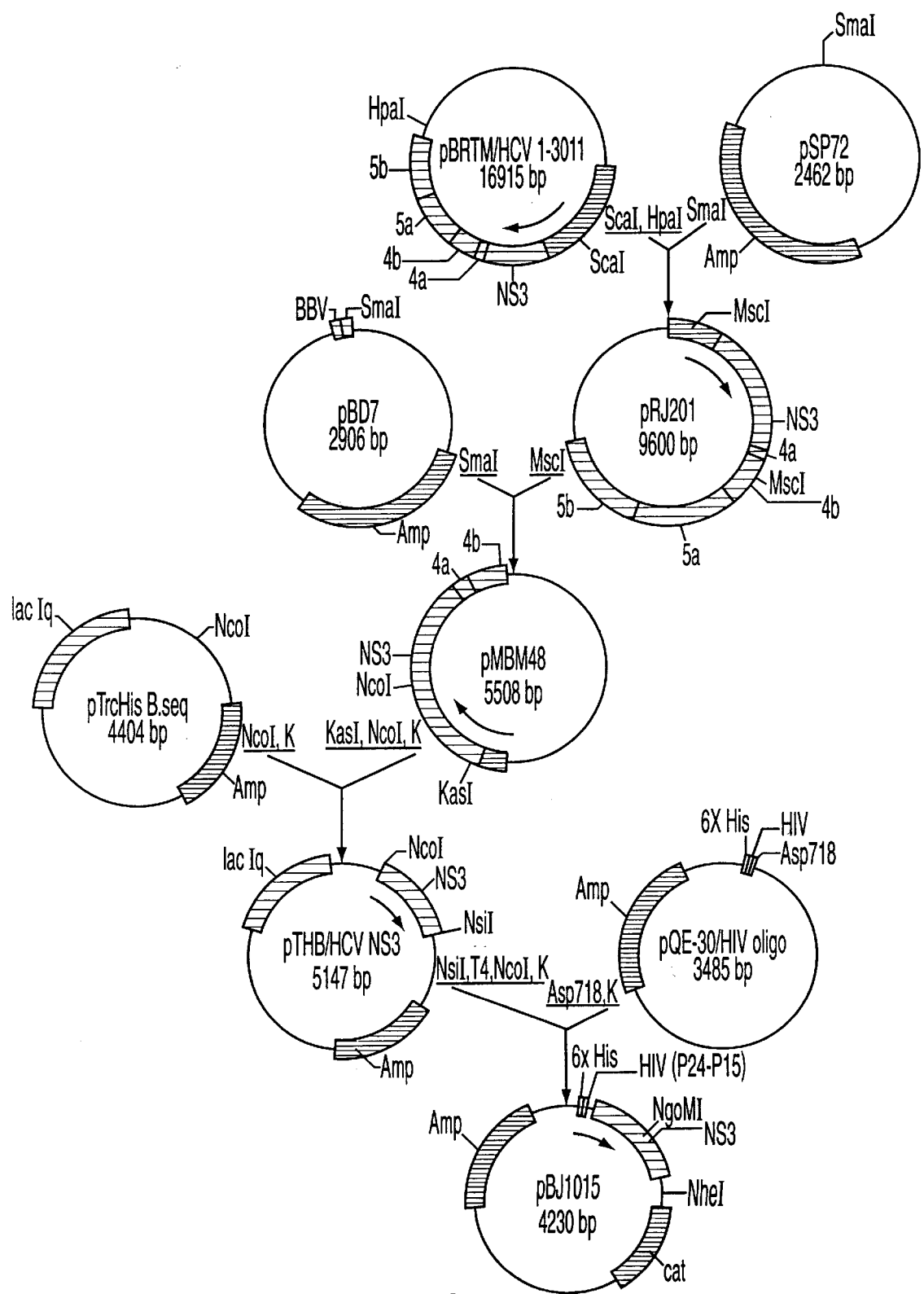
FIG. 2 depicts the recombinant synthesis of plasmid pBJ1015.
Figure 3:
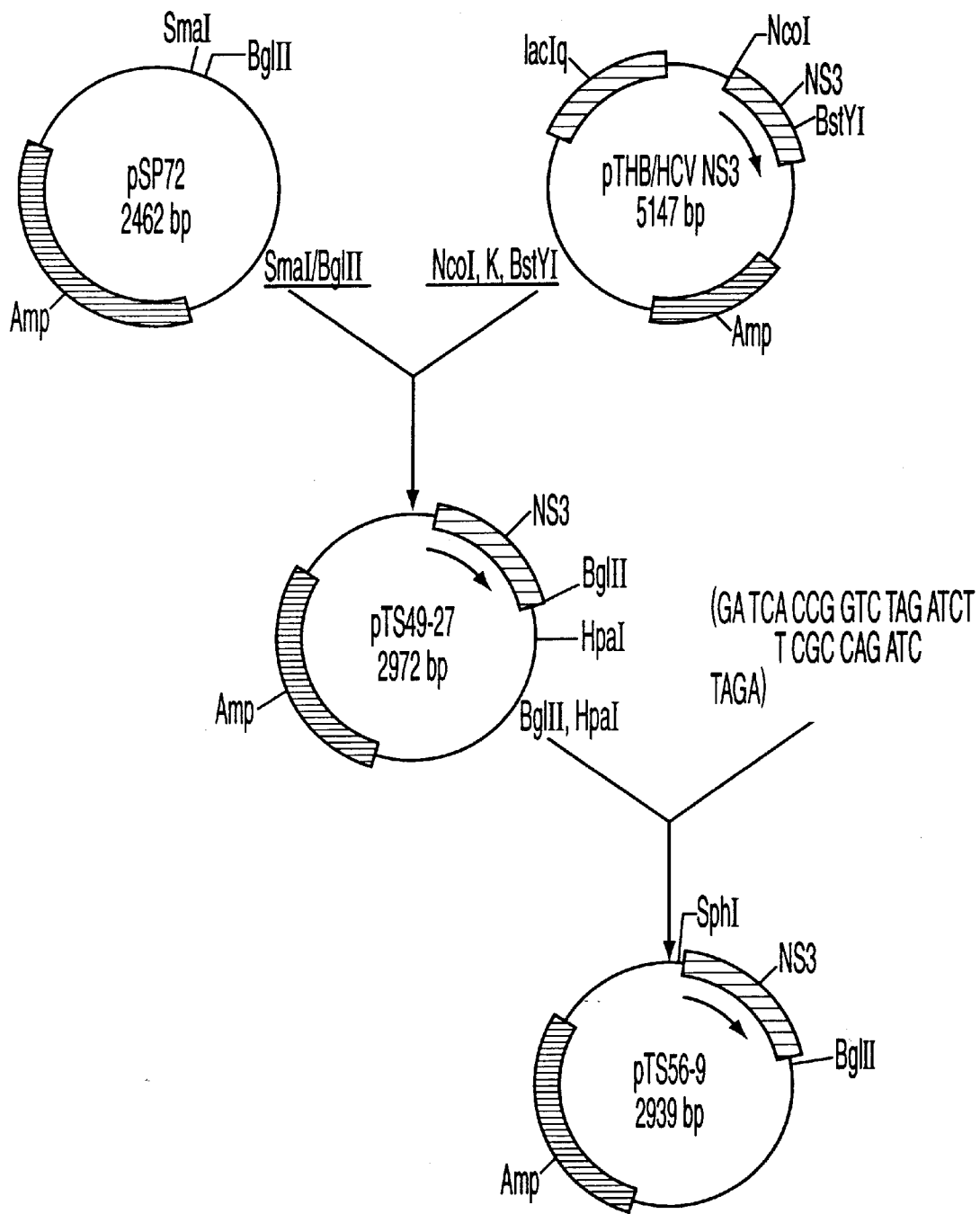
FIG. 3 depicts the recombinant synthesis of plasmid pTS56-9.

Several plasmids were designed and constructed using standard recombinant DNA techniques (Sambrook, Fritsch & Maniatis) to express the HCV protease in *E. coli* (FIG. 2–7). All HCV specific sequences originated from the parental plasmid pBRTM/HCV 1-3011 (Grakoui et al. 1993). To express the N-terminal 183 amino acid versions of the protease, a stop codon was inserted into the HCV genome using synthetic oligonucleotides (FIG. 3). The plasmids designed to express the N-terminal 246 amino acid residues were generated by the natural NcoI restriction site at the C-terminus.

i) Construction of the plasmid pBJ1015 (FIG. 2)

The plasmid pBRTM/HCV 1-3011 containing the entire HCV genome (Grakoui A., et al., *J. Virol.* 67: 1385–1395) was digested with the restriction enzymes Sca I and Hpa I and the 7138 bp (base pair) DNA fragment was isolated and cloned to the Sma I site of pSP72 (Promega) to produce the plasmid, pRJ201. The plasmid pRJ 201 was digested with Msc I and the 2106 bp Msc I fragment was isolated and cloned into the Sma I site of the plasmid pBD7. The resulting plasmid pMBM48 was digested with Kas I and Nco I, and the 734 bp DNA fragment after blunt ending with Klenow polymerase was isolated and cloned into Nco I digested, klenow polymerase treated pTrc HIS B seq expression plasmid (Invitrogen). The ligation regenerated a Nco I site at the 5' end and Nsi I site at the 3' end of HCV sequence. The plasmid pTHB HCV NS3 was then digested with Nco I and Nsi I, and treated with klenow polymerase and T4 DNA polymerase, to produce a blunt ended 738 bp DNA fragment which was isolated and cloned into Asp I cut, klenow polymerase treated expression plasmid pQE30 (HIV). The resulting plasmid pBJ 1015 expresses HCV NS3 (246 amino acids) protease.

(ii) Construction of the plasmid pTS 56-9 with a stop codon after amino acid 183 (FIG. 3)

The plasmid pTHB HCV NS3 was digested with Nco I, treated with klenow polymerase, then digested with Bst Y I; and the DNA fragment containing HCV sequence was isolated and cloned into Sma I and Bgl II digested pSP72. The resulting plasmid pTS 49-27 was then digested with Bgl II and Hpa I and ligated with a double stranded oligonucleotide:

GA TCA CCG GTC TAG ATCT    (SEQ ID NO: 18)

T GGC CAG ATC TAGA    (SEQ ID NO: 31)

Thus, a stop codon was placed directly at the end of DNA encoding the protease catalytic domain of the NS3 protein. This enabled the HCV protease to be expressed independently from the helicase domain of the NS3 protein.

Figure 4:
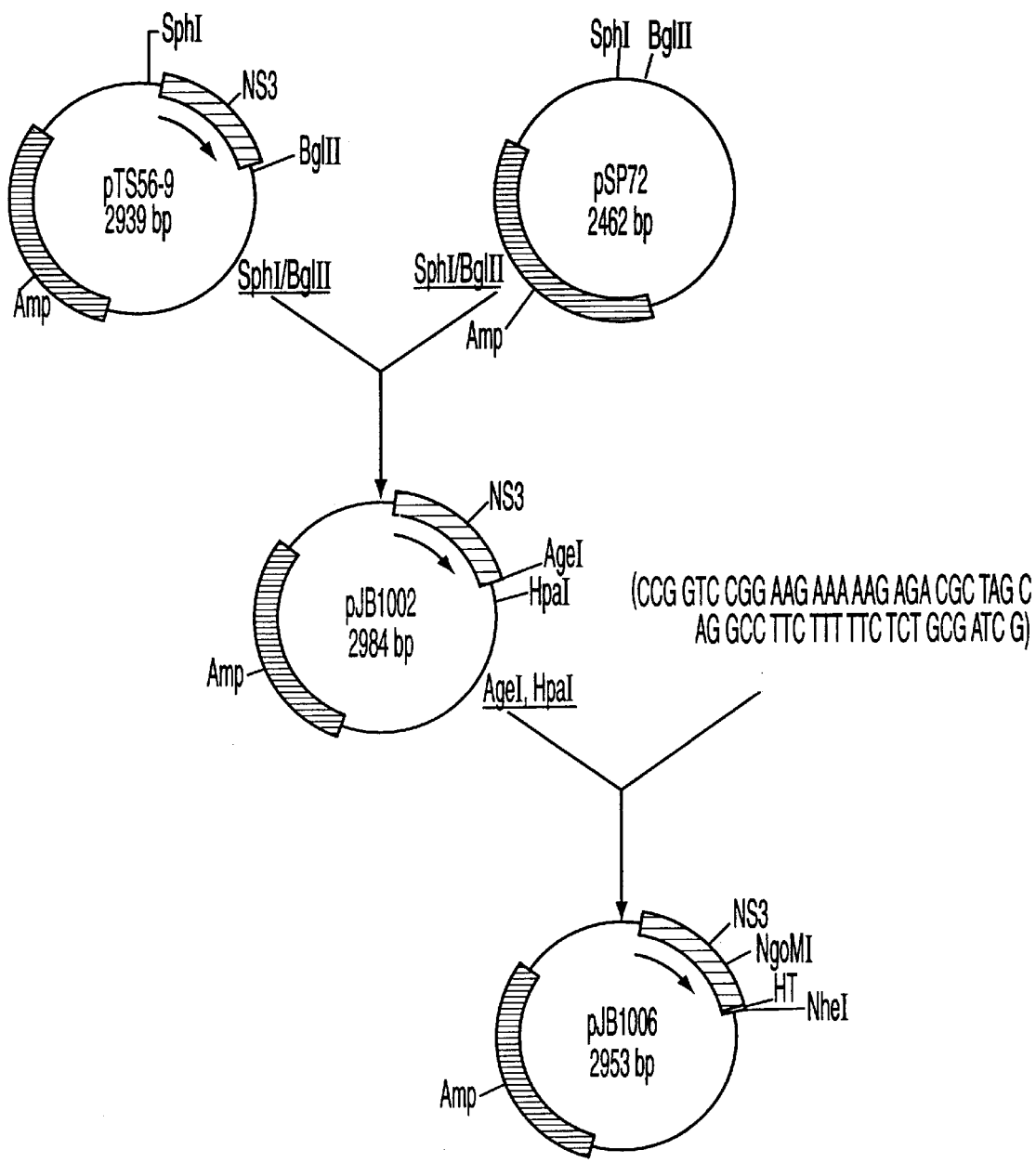
FIG. 4 depicts the recombinant synthesis of plasmid pJB1006.

(iii) Construction of the plasmid pJB 1006 Fused with a peptide of positively charged amino acids at the carboxy terminus of NS3 183 (FIG. 4).

The plasmid pTS 56-9 was digested with Sph I and Bgl II and the DNA fragment containing HCV sequence was isolated and cloned into a Sph I, Bgl II cut pSP72. The resulting plasmid pJB 1002 digested with Age I and HpaI and ligated to a double stranded oligonucleotide, (SEQ ID NO. 19)
CCG GTC CGG AAG AAA AAG AGA CGC TAG C

AG GCC TTC TTT TTC TCT GCG ATC G (SEQ ID NO: 32), to construct pJB 1006. This fused the hydrophilic, solubilizing motif onto the NS3 protease.

Figure 5:
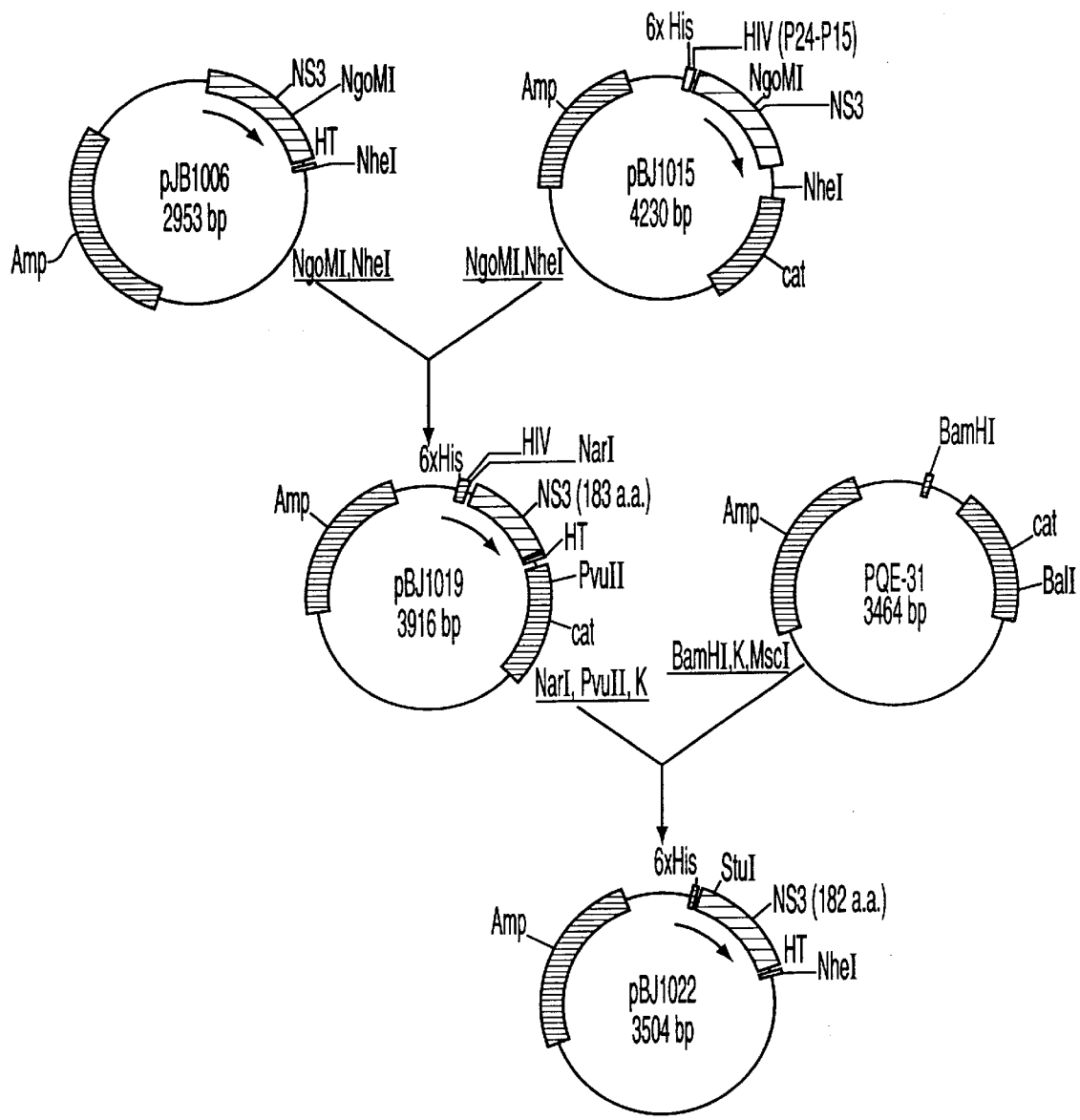
FIG. 5 depicts the recombinant synthesis of plasmid pBJ1022.

(iv) Construction of the plasmid pBJ 1022 expressing His-NS3(183)-HT in *E. coli* (FIG. 5)

The plasmid pJB 1006 was digested with NgoM I and Nhe I and the 216 bp DNA fragment was isolated and cloned into Ngo M I, Nhe I cut pBJ 1015 to construct plasmid pBJ 1019. The plasmid pBJ 1019 was digested with Nar I and Pvu II, and treated with Klenow polymerase to fill in 5' ends of Nar I fragments. The expression plasmid pQE31 (Invitrogen) was digested with BamH I, blunt ended with Klenow polymerase. The 717 bp Nar I-Pvu II DNA fragment was isolated and ligated to the 2787 bp BamH I/Klenowed-Msc I (Bal I) fragment of the expression plasmid pQE31 (Invitrogen). The recombinant plasmid, pBJ 1022, obtained after transformation into E. coli expresses His NS3(2-183)-HT which does not contain any HIV protease cleavage site sequence. The plasmid also contains a large deletion in the CAT (Chloramphenicol Acetyl Transferase) gene.

Figure 6:
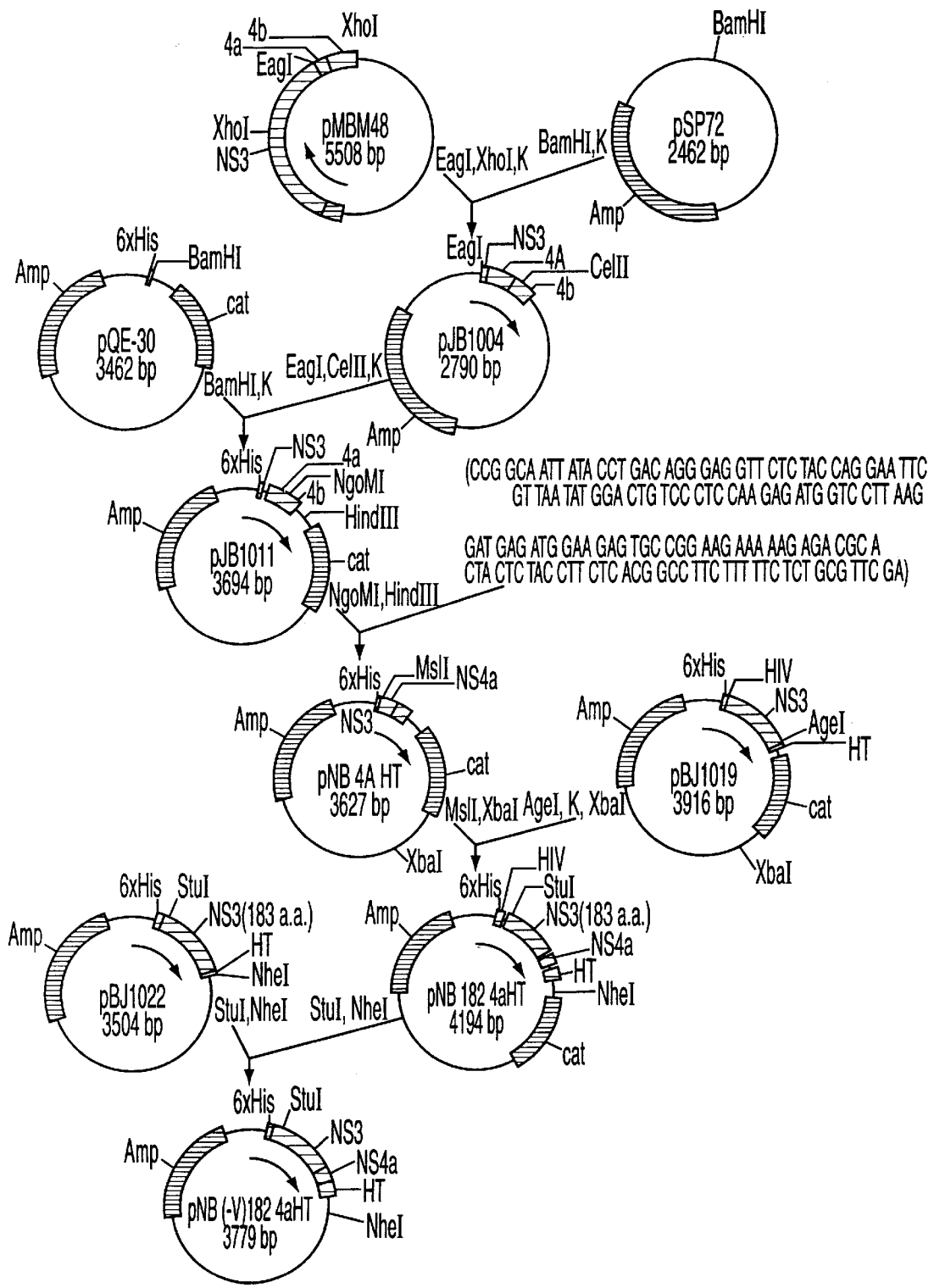
FIG. 6 depicts the recombinant synthesis of plasmid pNB(−V)182Δ4AHT.

(v) Construction of the plasmid pNB(-V)182-Δ4A HT (FIG. 6)

The plasmid pMBM 48 was digested with Eag I and Xho I, treated with Klenow polymerase and the 320 bp DNA fragment was isolated and cloned into BamH I cut, blunt ended pSP 72 to construct the plasmid pJB1004. The 320 bp fragment encodes 7 amino acid from carboxy terminal of NS3(631), all of NS4A, and the amino terminal 46 amino acid of NS4B. The recombinant plasmid pJB1004 was digested with Eag I and Cel 2, blunt ended with Klenow polymerase. The 220 bp DNA fragment was isolated and cloned into the expression plasmid pQE30 which was digested with BamH I and blunt ended with Klenow polymerase prior to ligation. The resulting plasmid pJB 1011 was digested with NgoM I and Hind III and ligated to a double stranded oligonucleotide,

```
CCG GCA ATT ATA CCT GAC AGG GAG GTT CTC TAC CAG GAA TTC   (SEQ ID NO: 20)
    GT TAA TAT GGA CTG TCC CTC CAA GAG ATG GTC CTT AAG   (SEQ ID NO: 32)
GAT GAG ATG GAA GAG TGC CGG AAG AAA AAG AGA CGC A
CTA CTC TAC CTT CTC ACG GCC TTC TTT TTC TCT GCG TTG GA
``` to construct the plasmid pNB 4A HT. The plasmid pNB 4AHT was digested with Msl I and Xba I. The 1218 bp DNA fragment was isolated and cloned into Age I cut, kienow polymerase treated, Xba I cut vector DNA of pBJ 1019. The ligation results in a substitution of the 183rd amino acid residue valine by a glycine residue in NS3, and a deletion of amino terminal three amino acid residues of NS4A at the junction. The recombinant plasmid pNB182Δ4A HT comprising NS3(182aa)-G-NS4A(4-54 amino acid) does not contain NS3/NS4A cleavage site sequence at the junction and is not cleaved by the autocatalytic activity of NS3. Finally the plasmid pNB182Δ4A HT (SEQ ID NO 8) was digested with Stu I and Nhe I, the 803 bp DNA fragment was isolated and cloned into Stu I and Nhe I cut plasmid pBJ 1022. The resulting plasmid pNB(-V)182-Δ4A HT contains a deletion of the HIV sequence from the amino terminus end of the NS3 sequence and in the CAT gene (SEQ ID NO 23).

Figure 7:
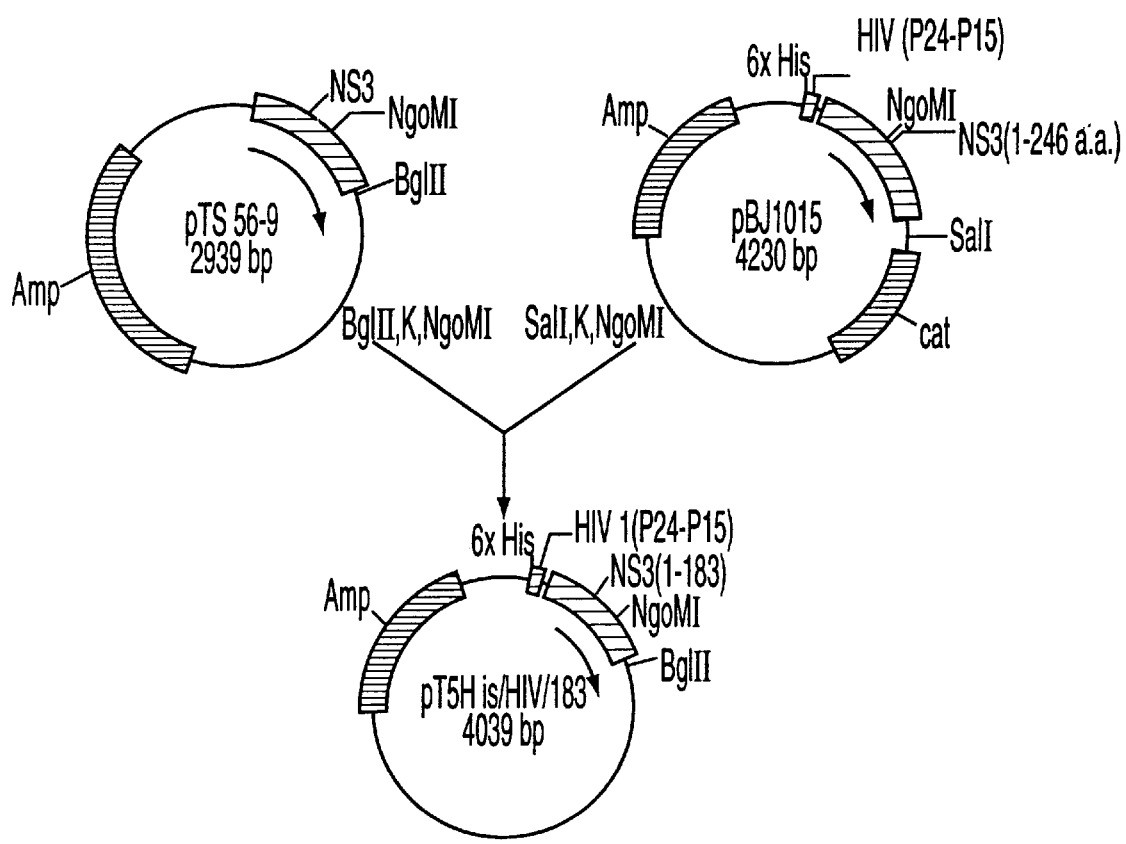
FIG. 7 depicts the recombinant synthesis of plasmid pT5His/HIV/183.

(vi) Construction of the plasmid pT5 His HIV-NS3 (FIG. 7)

The plasmid pTS56-9 was digested with Bgl II, and treated with Klenow polymerase to fill in 5' ends. The plasmid was then digested with NgoM I and the blunt ended Bgl II/NgoMI fragment containing the NS3 sequence was isolated and ligated to the SglI, Klenow treated NgmMI cut and Sal I klenowed pBJ 1015. The resulting plasmid is designated pT5His HIV 183.

EXAMPLE 4

Purification of HCV NS3 Protease having a Solubilizing Motif

Purification of His182HT (SEQ ID NO 4) and His (-V)182Δ4AHT (SEQ ID NO 8)

The recombinant plasmids pBJ1022 and pNB(-V) 182Δ4A were used to transform separate cultures of E. coli strain M15 [pREP4] (Qiagen), which over-expresses the lac repressor, according to methods recommended by the manufacturer. M15 [pREP4] bacteria harboring recombinant plasmids were grown overnight in broth containing 20 g/L bactotrypton, 10 g/L bacto-yeast extract, 5 g/L NaCl (20-10-5 broth) and supplemented with 100 μg/ml ampicillin and 25 μg/ml kanamycin. Cultures were diluted down to O.D.600 of 0.1, then grown at 30° C. to O.D.600 of 0.6 to 0.8, after which IPTG was added to a final concentration of 1 mM. At post-induction 2 to 3 hours, the cells were harvested by pelleting, and the cell pellets were washed with 100 mM Tris, pH 7.5. Cell lysates were prepared as follows: to each ml equivalent of pelleted fermentation broth was added 50 μl sonication buffer (50 mM sodium phosphate, pH 7.8, 0.3M NaCl) with 1 mg/ml lysozyme; cell suspension was placed on ice for 30 min. Suspension was then brought to a final concentration of 0.2% Tween-20, 10 mM dithiothreitol (DTT), and sonicated until cell breakage was complete. Insoluble material was pelleted at 12,000×g in a microcentrifuge for 15 minutes, the soluble portion was removed to a separate tube and the soluble lysate was then brought to a final concentration of 10% glycerol. Soluble lysates from cells expressing the plasmids produce strongly immunoreactive bands of the predicted molecular weight. Soluble lysates prepared for $Ni^{2+}$ column purification were prepared with 10 mM β-mercaptoethanol (BME) instead of DTT. Lysates were stored at −80° C.

Purification using $Ni^{2+}$-Nitrosyl acetic acid (NTA) agarose (QIAGEN)

The proteins were then purified by placing the extracted lysate on an NTA agarose column. NTA agarose column chromatography was used because the histidine tag which was fused to the N-terminus of the proteases readily binds to the nickel column. This produces a powerful affinity chromatographic technique for rapidly purifying the soluble protease. The column chromatography was performed in a batch mode. The $Ni^{2+}$ NTA resin (3ml) was washed twice with 50 ml of Buffer A (50 mM sodium phosphate pH 7.8 containing 10% glycerol, 0.2% Tween20, 10 mM BME). The lysate obtained from a 250 ml fermentation (12.5 ml) was incubated with the resin for one hour at 4° C. The flow through was collected by centrifugation. The resin was packed into a 1.0×4 cm column and washed with buffer A until the baseline was reached. The bound protein was then eluted with a 20 ml gradient of imidazole (0–20 0.5M) in buffer A. Eluted fractions were evaluated by SDS-PAGE and western blot analysis using a rabbit polyclonal antibody to His-HIV 183.

Purification using POROS metal-chelate Affinity Column

In an alternative method to purify the proteins the lysate containing the proteins were applied to a POROS metal-chelate affinity column. Perfusion chromatography was performed on a POROS MC metal chelate column (4.6×50 mm, 1.7 ml) precharged with $Ni^{2+}$. The sample was applied at 10 ml/min and the column was washed with buffer A. The column was step eluted with ten column volumes of buffer A containing 25 mM imidazole. The column was further eluted with a 25 column volume gradient of 25–250 mM imidazole in buffer A. All eluted fractions were evaluated by SDS-PAGE and western blot analysis using rabbit polyclonal antibody.

EXAMPLE 5

Peptide Synthesis of the 5A/5B and 4B/5A Substrates

The peptides 5A/5B and 4B/5A substrates (SEQ ID NOs 16, 18, 19, 20 and 21) were synthesized using Fmoc chemistry on an ABI model 431A peptide synthesizer. The manufacture recommended FastMoc™ activation strategy (HBTU/HOBt) was used for the synthesis of 4A activator peptide. A more powerful activator, HATU with or without the additive HOAt were employed to assemble 5A/5B substrate peptides on a preloaded Wang resin. The peptides were cleaved off the resin and deprotected by standard TFA cleavage protocol. The peptides were purified on reverse phase HPLC and confirmed by mass spectrometric analysis.

EXAMPLE 6

HPLC-assay using a Synthetic 5A/5B Peptide Substrate

To test the proteolytic activity of the HCV NS3 protease the DTEDVVCC SMSYTWTGK (SEQ ID NO 16) and soluble HCV NS3 (SEQ ID NO 27) were placed together in an assay buffer. The assay buffer was 50 mM sodium phosphate pH 7.8, containing 15% glycerol, 10 mM DTT, 0.2% Tween20 and 200 mM NaCl). The protease activity of SEQ ID NO 27 cleaved the substrate into two byproduct peptides, namely 5A and 5B. The substrate and two byproduct peptides were separated on a reversed-phase HPLC column. (Dynamax, 4.6×250 mm) with a pore size of 300 Å and a particle size of 5 μm. The column was equilibrated with 0.1%TFA (Solvent A) at a flow rate of 1 ml per minute. The substrate and the product peptide standards were applied to the column equilibrated in A. Elution was performed with a acetonitrile gradient (Solvent B=100% acetonitrile in A). Two gradients were used for elution (5% to 70% B in 50 minutes followed by 70% to 100% B in 10 minutes).

```
                        SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
         (A) LENGTH: 21 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY:
         (D) OTHER INFORMATION: Xaa is aminocaproic acid (Acp).

(xi) SEQUENCE DESCRIPTION: SEQ ID NO:1:

Glu Asp Val Val Cys Cys Xaa Xaa Cys Val Val Ile Val Gly Arg Ile
 1               5                  10                  15

Val Leu Ser Gly Lys
            20

(2) INFORMATION FOR SEQ ID NO:2:

(i) SEQUENCE CHARACTERISTICS:
         (A) LENGTH: 21 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY:
         (D) OTHER INFORMATION: Xaa is aminocaproic acid (Acp).

(xi) SEQUENCE DESCRIPTION: SEQ ID NO:2:

Glu Asp Val Val Cys Cys Xaa Val Val Ile Val Gly Arg Ile Val
 1               5                  10                  15

Leu Ser Gly Lys Lys
            20
```

```
(2) INFORMATION FOR SEQ ID NO:3:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (D) OTHER INFORMATION: Xaa is aminocaproic acid (Acp).

(xi) SEQUENCE DESCRIPTION: SEQ ID NO:3:

Glu Asp Val Val Cys Cys Xaa Lys Lys Gly Ser Leu Val Ile Arg Gly
 1               5                  10                  15

Val Ile Val Val Cys
            20

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (D) OTHER INFORMATION: Xaa is lysine having a peptide bond
            between its e-amino group and the carboxyl group of
            lysine at position 8.  The carboxyl group of the Xaa
            forms a peptide bond with the a-amino group of another
            lysine (not shown);

(xi) SEQUENCE DESCRIPTION: SEQ ID NO:4:

Glu Asp Val Val Cys Cys Xaa Lys Gly Ser Leu Val Ile Arg Gly Val
 1               5                  10                  15

Ile Val Val Cys
            20

(2) INFORMATION FOR SEQ ID NO:5:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (D) OTHER INFORMATION:  Xaa is aminocaproic acid (Acp).
            Amino acid residues at positions 9-21 are preferably
            D-amino acid residues;

(xi) SEQUENCE DESCRIPTION: SEQ ID NO:5:

Glu Asp Val Val Cys Cys Xaa Xaa Lys Gly Ser Leu Val Ile Arg Gly
 1               5                  10                  15

Val Ile Val Val Cys
            20

(2) INFORMATION FOR SEQ ID NO:6:

(i) SEQUENCE CHARACTERISTICS:
        (A) LENGTH: 21 amino acids
        (B) TYPE: amino acid
```

(C) STRANDEDNESS: single
        (D) TOPOLOGY: linear (ii) MOLECULE TYPE: peptide (ix) FEATURE:
        (A) NAME/KEY:
        (D) OTHER INFORMATION: Xaa is aminocaproic acid (Acp).
            The lysine residue at position 8 has a peptide bond
            between the carboxyl group of Acp and the a amino group
            of the lysine, and the e amino group of the lysine at
            position 8 forms a peptide bond with the carboxyl group
            of the cysteine residue at position 9 and the amino acid
            residues at positions 9-21 are preferably D-amino acid
            residues;

(xi) SEQUENCE DESCRIPTION: SEQ ID NO:6:

Glu Asp Val Val Cys Cys Xaa Lys Cys Val Val Ile Val Gly Arg Ile
1               5                   10                  15

Val Leu Ser Gly Lys
            20

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (D) OTHER INFORMATION: Xaa is aminocaproic acid (Acp).
            Amino acids at positions 8-20 are preferably D-amino
            acids.

(xi) SEQUENCE DESCRIPTION: SEQ ID NO:7:

Glu Asp Val Val Cys Cys Xaa Lys Gly Ser Leu Val Ile Arg Gly Val
1               5                   10                  15

Ile Val Val Cys Lys
            20

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (D) OTHER INFORMATION: Xaa is a lysine wherein
            the e amino group of which forms a peptide bond with the
            carboxyl group of the cysteine residue at position 8 and
            the carboxyl group of the lysine residue forms a peptide
            bond with an a amino group of another lysine residue (not
            shown), preferably the amino acid residues at positions
            8 - 20 are D- amino acid residues.

(xi) SEQUENCE DESCRIPTION: SEQ ID NO:8:

Glu Asp Val Val Cys Cys Xaa Cys Val Val Ile Val Gly Arg Ile Val
1               5                   10                  15

Leu Ser Gly Lys
            20

(2) INFORMATION FOR SEQ ID NO:9:

```
        (i) SEQUENCE CHARACTERISTICS:
             (A) LENGTH: 14 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY:
             (D) OTHER INFORMATION: The amino acid residues at
                 positions 1- 13 are preferably D-amino acid residues and
                 lysine at position 14 is preferably an L-amino acid
                 residue;

(xi) SEQUENCE DESCRIPTION: SEQ ID NO:9:

Lys Gly Ser Leu Val Ile Arg Gly Val Ile Val Val Cys Lys
1               5                   10

(2) INFORMATION FOR SEQ ID NO:10:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY:
             (D) OTHER INFORMATION: Amino acid residues at positions 1 - 11
                 are preferably D-amino acids;

(xi) SEQUENCE DESCRIPTION: SEQ ID NO:10:

Lys Gly Ser Leu Val Ile Arg Gly Val Ile Val Lys
1               5                   10

(2) INFORMATION FOR SEQ ID NO:11:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY:
             (D) OTHER INFORMATION: The amino acid residues are
                 preferably D-amino acid residues.

(xi) SEQUENCE DESCRIPTION: SEQ ID NO:11:

Cys Val Val Ile Val Gly Arg Ile Val Leu Ser Gly
1               5                   10

(2) INFORMATION FOR SEQ ID NO:12:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY:
             (D) OTHER INFORMATION: The amino acid residues are
                 preferably D-amino acids and the serine residue at
                 position 1 is preferably acetylated.
```

(xi) SEQUENCE DESCRIPTION: SEQ ID NO:12:

Ser Leu Val Ile Arg Gly Val Ile Val
1               5

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (D) OTHER INFORMATION: The amino acid residues are
            preferably D-amino acid residues and the lysine
            residue at position 1 is preferably acetylated.

(xi) SEQUENCE DESCRIPTION: SEQ ID NO:13:

Lys Gly Ser Leu Val Ile Arg Gly Val Ile Val Val Cys
1               5                   10

(2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (D) OTHER INFORMATION: Lys at position 1 is bound to
            biotin and the amino acid residues at positions 2 - 14
            are preferably D-amino acids.

(xi) SEQUENCE DESCRIPTION: SEQ ID NO:14:

Lys Gly Ser Leu Val Ile Arg Gly Val Ile Val Val Cys Lys Lys
1               5                   10                  15

(2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY:
        (D) OTHER INFORMATION: Xaa is a lysine residue in which
            the e amino group of the lysine forms a peptide bond with
            a biotin and amino acid residues at positions 1 - 13 are
            preferably D-amino acid residues.

(xi) SEQUENCE DESCRIPTION: SEQ ID NO:15:

Lys Gly Ser Leu Val Ile Arg Gly Val Ile Val Val Cys Xaa Lys
1               5                   10                  15

(2) INFORMATION FOR SEQ ID NO:16:

(i) SEQUENCE CHARACTERISTICS:
        (A) LENGTH: 549 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: HCV NS3 Protease (ix) FEATURE:
    (A) NAME/KEY: CDS
    (B) LOCATION: 1..549

(xi) SEQUENCE DESCRIPTION: SEQ ID NO:16:

| | | | | | | | | | | | | | | | | |
|---|---|---|---|---|---|---|---|---|---|---|---|---|---|---|---|---|
| GCG | CCC | ATC | ACG | GCG | TAC | GCC | CAG | CAG | ACG | AGA | GGC | CTC | CTA | GGG | TGT | 48 |
| Ala | Pro | Ile | Thr | Ala | Tyr | Ala | Gln | Gln | Thr | Arg | Gly | Leu | Leu | Gly | Cys | |
| 1 | | | | 5 | | | | | 10 | | | | | 15 | | |
| ATA | ATC | ACC | AGC | CTG | ACT | GGC | CGG | GAC | AAA | AAC | CAA | GTG | GAG | GGT | GAG | 96 |
| Ile | Ile | Thr | Ser | Leu | Thr | Gly | Arg | Asp | Lys | Asn | Gln | Val | Glu | Gly | Glu | |
| | | | 20 | | | | | 25 | | | | | 30 | | | |
| GTC | CAG | ATC | GTG | TCA | ACT | GCT | ACC | CAA | ACC | TTC | CTG | GCA | ACG | TGC | ATC | 144 |
| Val | Gln | Ile | Val | Ser | Thr | Ala | Thr | Gln | Thr | Phe | Leu | Ala | Thr | Cys | Ile | |
| | | | 35 | | | | | 40 | | | | | 45 | | | |
| AAT | GGG | GTA | TGC | TGG | ACT | GTC | TAC | CAC | GGG | GCC | GGA | ACG | AGG | ACC | ATC | 192 |
| Asn | Gly | Val | Cys | Trp | Thr | Val | Tyr | His | Gly | Ala | Gly | Thr | Arg | Thr | Ile | |
| | | 50 | | | | | 55 | | | | | 60 | | | | |
| GCA | TCA | CCC | AAG | GGT | CCT | GTC | ATC | CAG | ATG | TAT | ACC | AAT | GTG | GAC | CAA | 240 |
| Ala | Ser | Pro | Lys | Gly | Pro | Val | Ile | Gln | Met | Tyr | Thr | Asn | Val | Asp | Gln | |
| 65 | | | | | 70 | | | | | 75 | | | | | 80 | |
| GAC | CTT | GTG | GGC | TGG | CCC | GCT | CCT | CAA | GGT | TCC | CGC | TCA | TTG | ACA | CCC | 288 |
| Asp | Leu | Val | Gly | Trp | Pro | Ala | Pro | Gln | Gly | Ser | Arg | Ser | Leu | Thr | Pro | |
| | | | | 85 | | | | | 90 | | | | | 95 | | |
| TGC | ACC | TGC | GGC | TCC | TCG | GAC | CTT | TAC | CTG | GTT | ACG | AGG | CAC | GCC | GAC | 336 |
| Cys | Thr | Cys | Gly | Ser | Ser | Asp | Leu | Tyr | Leu | Val | Thr | Arg | His | Ala | Asp | |
| | | | | 100 | | | | | 105 | | | | | 110 | | |
| GTC | ATT | CCC | GTG | CGC | CGG | CGA | GGT | GAT | AGC | AGG | GGT | AGC | CTG | CTT | TCG | 384 |
| Val | Ile | Pro | Val | Arg | Arg | Arg | Gly | Asp | Ser | Arg | Gly | Ser | Leu | Leu | Ser | |
| | | | 115 | | | | | 120 | | | | | 125 | | | |
| CCC | CGG | CCC | ATT | TCC | TAC | CTA | AAA | GGC | TCC | TCG | GGG | GGT | CCG | CTG | TTG | 432 |
| Pro | Arg | Pro | Ile | Ser | Tyr | Leu | Lys | Gly | Ser | Ser | Gly | Gly | Pro | Leu | Leu | |
| | | 130 | | | | | 135 | | | | | 140 | | | | |
| TGC | CCC | GCG | GGA | CAC | GCC | GTG | GGC | CTA | TTC | AGG | GCC | GCG | GTG | TGC | ACC | 480 |
| Cys | Pro | Ala | Gly | His | Ala | Val | Gly | Leu | Phe | Arg | Ala | Ala | Val | Cys | Thr | |
| 145 | | | | | 150 | | | | | 155 | | | | | 160 | |
| CGT | GGA | GTG | ACC | AAG | GCG | GTG | GAC | TTT | ATC | CCT | GTG | GAG | AAC | CTA | GAG | 528 |
| Arg | Gly | Val | Thr | Lys | Ala | Val | Asp | Phe | Ile | Pro | Val | Glu | Asn | Leu | Glu | |
| | | | | 165 | | | | | 170 | | | | | 175 | | |
| ACA | ACC | ATG | AGA | TCC | CCG | GTG | | | | | | | | | | 549 |
| Thr | Thr | Met | Arg | Ser | Pro | Val | | | | | | | | | | |
| | | | | 180 | | | | | | | | | | | | |

(2) INFORMATION FOR SEQ ID NO:17:

(i) SEQUENCE CHARACTERISTICS:
    (A) LENGTH: 162 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: NS4A (ix) FEATURE:
    (A) NAME/KEY: CDS
    (B) LOCATION: 1..162

(xi) SEQUENCE DESCRIPTION: SEQ ID NO:17:

```
AGC ACC TGG GTG CTC GTT GGC GGC GTC CTG GCT GCT CTG GCC GCG TAT        48
Ser Thr Trp Val Leu Val Gly Gly Val Leu Ala Ala Leu Ala Ala Tyr
 1               5                  10                  15

TGC CTG TCA ACA GGC TGC GTG GTC ATA GTG GGC AGG ATT GTC TTG TCC        96
Cys Leu Ser Thr Gly Cys Val Val Ile Val Gly Arg Ile Val Leu Ser
                 20                  25                  30

GGG AAG CCG GCA ATT ATA CCT GAC AGG GAG GTT CTC TAC CAG GAG TTC       144
Gly Lys Pro Ala Ile Ile Pro Asp Arg Glu Val Leu Tyr Gln Glu Phe
         35                  40                  45

GAT GAG ATG GAA GAG TGC                                               162
Asp Glu Met Glu Glu Cys
     50
```

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
GATCACCGGT CTAGATCT                                                    18
```

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
CCGGTCCGGA AGAAAAAGAG ACGCTAGC                                         28
```

(2) INFORMATION FOR SEQ ID NO:20:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

```
CCGGCAATTA TACCTGACAG GGAGGTTCTC TACCAGGAAT TCGATGAGAT GGAAGAGTGC      60

CGGAAGAAAA AGAGACGCA                                                   79
```

(2) INFORMATION FOR SEQ ID NO:21:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: NS4A Active Mutant (xi) SEQUENCE DESCRIPTION: SEQ ID NO:21:

Cys Val Val Ile Val Gly Arg Ile Val Leu Ser Gly Lys 5,990,276

29                                                                                                     30

-continued (2) INFORMATION FOR SEQ ID NO:22:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Soluble 5A/5B Substrate (xi) SEQUENCE DESCRIPTION: SEQ ID NO:22:

```
Asp Thr Glu Asp Val Val Cys Cys Ser Met Ser Tyr Thr Trp Thr Gly
1               5                   10                  15
Lys
```

(2) INFORMATION FOR SEQ ID NO:23:

(i) SEQUENCE CHARACTERISTICS:
        (A) LENGTH: 765 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: pNB1824AHT (ix) FEATURE:
        (A) NAME/KEY: CDS
        (B) LOCATION: 1..765

(xi) SEQUENCE DESCRIPTION: SEQ ID NO:23:

```
ATG AGA GGA TCG CAT CAC CAT CAC CAT CAC ACG GAT CCG CCC ATC ACG        48
Met Arg Gly Ser His His His His His His Thr Asp Pro Pro Ile Thr
1               5                   10                  15

GCG TAC GCC CAG CAG ACG AGA GGC CTC CTA GGG TGT ATA ATC ACC AGC        96
Ala Tyr Ala Gln Gln Thr Arg Gly Leu Leu Gly Cys Ile Ile Thr Ser
                20                  25                  30

CTG ACT GGC CGG GAC AAA AAC CAA GTG GAG GGT GAG GTC CAG ATC GTG       144
Leu Thr Gly Arg Asp Lys Asn Gln Val Glu Gly Glu Val Gln Ile Val
        35                  40                  45

TCA ACT GCT ACC CAA ACC TTC CTG GCA ACG TGC ATC AAT GGG GTA TGC       192
Ser Thr Ala Thr Gln Thr Phe Leu Ala Thr Cys Ile Asn Gly Val Cys
    50                  55                  60

TGG ACT GTC TAC CAC GGG GCC GGA ACG AGG ACC ATC GCA TCA CCC AAG       240
Trp Thr Val Tyr His Gly Ala Gly Thr Arg Thr Ile Ala Ser Pro Lys
65                  70                  75                  80

GGT CCT GTC ATC CAG ATG TAT ACC AAT GTG GAC CAA GAC CTT GTG GGC       288
Gly Pro Val Ile Gln Met Tyr Thr Asn Val Asp Gln Asp Leu Val Gly
                85                  90                  95

TGG CCC GCT CCT CAA GGT TCC CGC TCA TTG ACA CCC TGC ACC TGC GGC       336
Trp Pro Ala Pro Gln Gly Ser Arg Ser Leu Thr Pro Cys Thr Cys Gly
            100                 105                 110

TCC TCG GAC CTT TAC CTG GTT ACG AGG CAC GCC GAC GTC ATT CCC GTG       384
Ser Ser Asp Leu Tyr Leu Val Thr Arg His Ala Asp Val Ile Pro Val
        115                 120                 125

CGC CGG CGA GGT GAT AGC AGG GGT AGC CTG CTT TCG CCC CGG CCC ATT       432
Arg Arg Arg Gly Asp Ser Arg Gly Ser Leu Leu Ser Pro Arg Pro Ile
    130                 135                 140

TCC TAC CTA AAA GGC TCC TCG GGG GGT CCG CTG TTG TGC CCC GCG GGA       480
```

```
            Ser Tyr Leu Lys Gly Ser Ser Gly Gly Pro Leu Leu Cys Pro Ala Gly
            145                 150                 155                 160

CAC GCC GTG GGC CTA TTC AGG GCC GCG GTG TGC ACC CGT GGA GTG ACC            528
His Ala Val Gly Leu Phe Arg Ala Ala Val Cys Thr Arg Gly Val Thr
                165                 170                 175

AAG GCG GTG GAC TTT ATC CCT GTG GAG AAC CTA GAG ACA ACC ATG AGA            576
Lys Ala Val Asp Phe Ile Pro Val Glu Asn Leu Glu Thr Thr Met Arg
            180                 185                 190

TCC CCG GGG GTG CTC GTT GGC GGC GTC CTG GCT GCT CTG GCC GCG TAT            624
Ser Pro Gly Val Leu Val Gly Gly Val Leu Ala Ala Leu Ala Ala Tyr
        195                 200                 205

TGC CTG TCA ACA GGC TGC GTG GTC ATA GTG GGC AGG ATT GTC TTG TCC            672
Cys Leu Ser Thr Gly Cys Val Val Ile Val Gly Arg Ile Val Leu Ser
        210                 215                 220

GGG AAG CCG GCA ATT ATA CCT GAC AGG GAG GTT CTC TAC CAG GAG TTC            720
Gly Lys Pro Ala Ile Ile Pro Asp Arg Glu Val Leu Tyr Gln Glu Phe
225                 230                 235                 240

GAT GAG ATG GAA GAG TGC CGG AAG AAA AAG AGA CGC AAG CTT AAT               765
Asp Glu Met Glu Glu Cys Arg Lys Lys Lys Arg Arg Lys Leu Asn
                245                 250                 255
```

(2) INFORMATION FOR SEQ ID NO:24:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Native NS4A (ix) FEATURE:
        (A) NAME/KEY: CDS
        (B) LOCATION: 1..162

(xi) SEQUENCE DESCRIPTION: SEQ ID NO:24:

```
TCA ACA TGG GTG CTC GTT GGC GGC GTC CTG GCT GCT CTG GCC GCG TAT            48
Ser Thr Trp Val Leu Val Gly Gly Val Leu Ala Ala Leu Ala Ala Tyr
1                   5                   10                  15

TGC CTG TCA ACA GGC TGC GTG GTC ATA GTG GGC AGG ATT GTC TTG TCC            96
Cys Leu Ser Thr Gly Cys Val Val Ile Val Gly Arg Ile Val Leu Ser
            20                  25                  30

GGG AAG CCG GCA ATT ATA CCT GAC AGG GAG GTT CTC TAC CAG GAG TTC            144
Gly Lys Pro Ala Ile Ile Pro Asp Arg Glu Val Leu Tyr Gln Glu Phe
        35                  40                  45

GAT GAG ATG GAA GAG TGC                                                    162
Asp Glu Met Glu Glu Cys
    50
```

(2) INFORMATION FOR SEQ ID NO:25:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Native 5A/5B Substrate (xi) SEQUENCE DESCRIPTION: SEQ ID NO:25:

Asp Thr Glu Asp Val Val Cys Cys Ser Met Ser Tyr Thr Trp Thr Gly

```
            1               5                10                15
```

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: NS3/NS4A Cleavage site (xi) SEQUENCE DESCRIPTION: SEQ ID NO:26:

```
Cys Met Ser Ala Asp Leu Glu Val Val Thr Ser Thr Trp Val Leu Val
1               5                  10                  15

Gly Gly Val Leu
            20
```

(2) INFORMATION FOR SEQ ID NO:27:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: NS4A/4B Cleavage Site (xi) SEQUENCE DESCRIPTION: SEQ ID NO:27:

```
Tyr Gln Glu Phe Asp Glu Met Glu Glu Cys Ser Gln His Leu Pro Tyr
1               5                  10                  15

Ile Glu Gln Gly
            20
```

(2) INFORMATION FOR SEQ ID NO:28:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: 4B/5A (xi) SEQUENCE DESCRIPTION: SEQ ID NO:28:

```
Trp Ile Ser Ser Glu Cys Thr Thr Pro Cys Ser Gly Ser Trp Leu Arg
1               5                  10                  15

Asp Ile Trp Asp
            20
```

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:

(A) NAME/KEY:
            (D) OTHER INFORMATION: Xaa is aminocaproic acid (Acp).

(xi) SEQUENCE DESCRIPTION: SEQ ID NO:29:

Glu Asp Val Val Cys Cys Xaa Lys
1               5

(2) INFORMATION FOR SEQ ID NO:30:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:30:

Cys Val Val Ile Val Gly Arg Ile Val Leu Ser Gly Lys
1               5                   10

(2) INFORMATION FOR SEQ ID NO:31:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:31:

AGATCTAGAC CGGT                                                             14

(2) INFORMATION FOR SEQ ID NO:32:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:32:

CCTAGCGTCT CTTTTTCTTC CGGA                                                  24

(2) INFORMATION FOR SEQ ID NO:33:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:33:

AGCTTGCGTC TCTTTTTCTT CCGGCACTCT TCCATCTCAT CGAATTCCTG GTAGAGAACC           60

TCCCTGTCAG GTATAATTG                                                        79

We claim:

1. A bivalent inhibitor of a hepatitis C NS3 protease comprised of a first peptide, a second peptide, and a linker, wherein said first peptide comprises a subsequence, a mutated subsequence or a mutated full-length sequence of a substrate of the hepatitis C NS3 protease which is not cleaved by the protease;

said second peptide comprises a subsequence of a hepatitis C NS4A polypeptide selected from the group consisting of SEQ ID NO: 9, SEQ ID NO: 10, SEQ ID NO: 11, SEQ ID NO: 12, SEQ ID NO: 13, SEQ ID NO: 14 and SEQ ID NO: 15; and said linker comprises a chemical entity capable of forming a bond with said first peptide and said second peptide and is equivalent in length to a carbon chain having about 7–14 carbon atoms.

2. The bivalent inhibitor of claim 1 selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

3. The bivalent inhibitor of claim 1, conjugated to a carrier protein.

4. The bivalent inhibitor of claim 3, wherein the carrier protein is selected from the group consisting of ovalbumin and serum albumin.

5. A monovalent inhibitor of a hepatitis C NS3 protease selected from the group consisting of SEQ ID NO: 9, SEQ ID NO: 10, SEQ ID NO: 11, SEQ ID NO: 12, SEQ ID NO: 13, SEQ ID NO: 14 and SEQ ID NO: 15.

6. The monovalent inhibitor of claim 5, conjugated to a carrier protein.

7. The monovalent inhibitor of claim 6, wherein the carrier protein is selected from the group consisting of ovalbumin and serum albumin.

* * * * *